United States Patent [19]
Blake et al.

[11] Patent Number: 5,203,698
[45] Date of Patent: Apr. 20, 1993

[54] WET FOAM SANDBLASTER

[76] Inventors: Thomas S. Blake, 115-A Railroad Ave.; Mark Fernwood, 1341 Camino Tassajara, both of Danville, Calif. 94526

[21] Appl. No.: 691,351

[22] Filed: Apr. 25, 1991

[51] Int. Cl.$^5$ .......................... A61C 3/02; A61C 1/10; A61C 1/12; A61C 15/00
[52] U.S. Cl. ........................................ 433/88; 433/84; 433/216; 51/319
[58] Field of Search ...................... 433/216, 88, 80, 84, 433/87; 51/319, 320, 321

[56] References Cited

U.S. PATENT DOCUMENTS

| | | | |
|---|---|---|---|
| 3,447,272 | 6/1969 | Eppler | 51/319 |
| 3,962,790 | 6/1976 | Riitano et al. | 433/81 |
| 3,971,136 | 7/1976 | Madsen | 433/88 |
| 4,214,871 | 6/1980 | Arnold | 433/216 |
| 4,412,402 | 11/1983 | Gallant | 51/439 |
| 4,595,365 | 6/1986 | Edel et al. | 433/216 |
| 4,776,794 | 10/1988 | Meller | 433/216 |
| 4,802,312 | 2/1989 | Glaeser et al. | 51/321 |
| 4,941,459 | 6/1990 | Mathur | 128/66 |
| 4,950,160 | 8/1990 | Karst | 433/88 |

Primary Examiner—Gene Mancene
Assistant Examiner—Cindy A. Cherichetti

[57] ABSTRACT

The subject matter of the disclosed invention relates generally to dental cleaning processes and apparatus. A "wet foam sandblasting" system is described below in which a bubble foam laden with abrasive particles is propelled through a small nozzle by gas pressure. The system has very specific applications in the dental industry for 1) general cleaning of teeth such as removal of tobacco, tea and other stains; 2) for selectively abrading away carious enamel, 3) cleaning prosthodontic restorations, 4) abrading various tooth and restorative materials in preparation for bonding, and 5) periodontal pocket cleaning with osteophylic abrasives; 6) cleaning of occlusal pits and fissures for sealing. In addition, the system has numerous applications in cleaning and etching materials in the jewelry, semi-conductor, automotive and other industries. The apparatus for cleaning teeth and other surfaces comprises a canister capable of being sealed and pressurized and receiving a mixture of liquid, abrasive particles and wetting agent, said canister also having a means to receive a stream of pressurized gas, a means to disperse pressurized gas into the mixture of liquid, abrasive particles and wetting agent causing thereby causing a formation of foam and urging the abrasive particles to become entrained into the foam, a means to direct the abrasive laden foam to the surface to be cleaned, and a means to control the flow of abrasive laden foam.

10 Claims, 3 Drawing Sheets

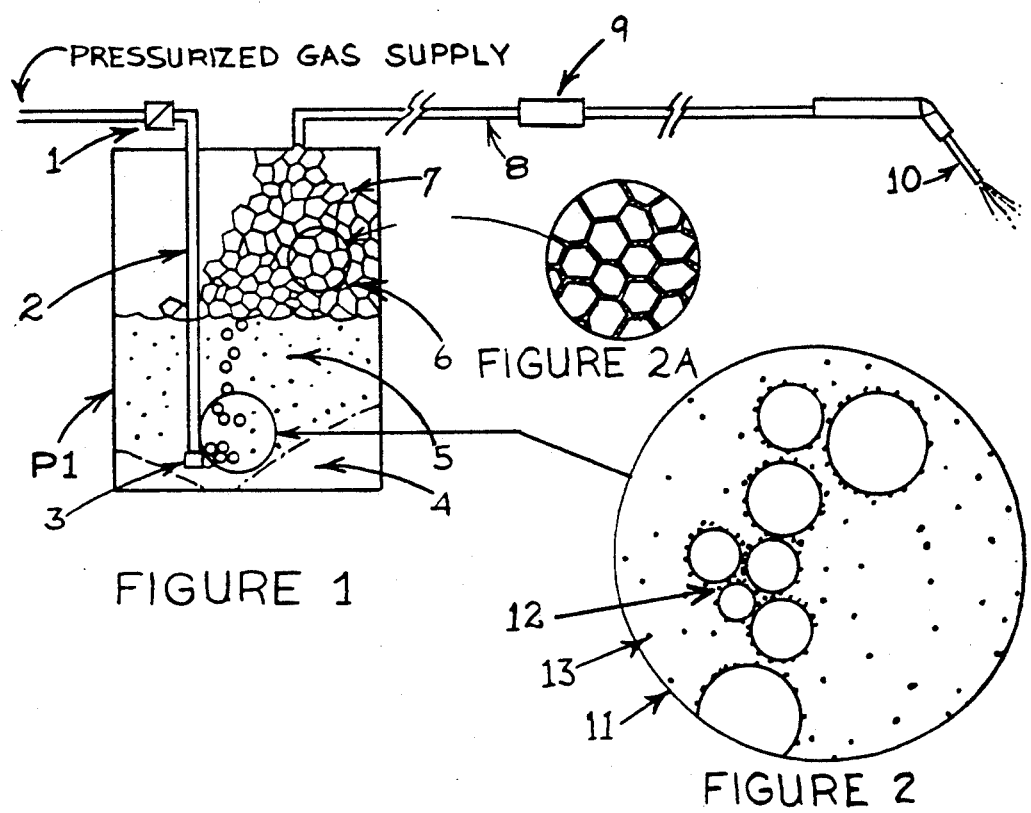

WET FOAM SANDBLASTER

BACKGROUND OF THE INVENTION

The subject matter of the disclosed invention relates generally to dental cleaning, abrading, etching, and cutting processes and apparatus. Prior art has instructed that dental cleaning may be accomplished through ultrasonic and mechanical sandblasting processes. Mixtures of high pressure fluids, including both liquids and gases, with abrasive particles, such as sand, are described in U.S. Pat. No. 2,133,149, Poncelet; U.S. Pat. No. 2,577,465, Jones; U.S. Pat. No. 2,744,361, Larson; and U.S. Pat. No. 4,369,607, Bruggeman et al. The referenced patents provide for a means to deliver a high pressure liquid stream mixed with large non-soluble abrasive particles delivered to a surface for cleaning or abrading.

Recently, the mixture of high pressure streams of liquid and abrasive for cleaning teeth has been envisioned. In U.S. Pat. No. 4,412,402, Gallant, an apparatus is disclosed which provides separate nozzles for ejection of a water stream and abrasive laden gas stream mixed at a point in the space between the nozzle orifice and the cleaning surface. One limitation of Gallant is that the distance between the apparatus and the cleaning surface must be carefully monitored so as to ensure proper mixture of the streams. Secondly, use of the Gallant apparatus suggests that abrasive particles not enveloped by the stream of liquid can be inhaled by a dental patient. In U.S. Pat. No. 4,595,365, Edel et al., the inventors have provided a means to mix a high pressure liquid stream and an abrasive in a way which overcomes some of the limitations of Gallant. Use of the apparatus disclosed in Edel still indicates that incomplete mixing of the liquid and abrasive particles occurs allowing airborne particles to be inhaled by a patient.

The apparatus disclosed in Gallant and Edel et al. both utilize pressurized air streams as a means to propel abrasive material toward the cleaning surface and a curtain of water. Deflection of the stream of water off the cleaning surface will result in both the dentist and the patient being splattered with the abrasive laden liquid. The deflected liquid is both a nuisance to the dentist and offensive to the patient.

Current sandblasters are limited as to the size of abrasive particles that may be used. Cracks, pits or fissures in dental and other surfaces may be smaller than the size of abrasive particles currently used in other sandblasters. This size limitation may result in incomplete cleaning or inadequate surface preparation for adhesive bonding procedures. Particles smaller than 20 microns can generally not be used effectively in existing sandblasters because of clumping due to moisture effects or because of static electrical charges which inhibit the flow of particles.

BRIEF DESCRIPTION OF THE INVENTION

A "wet foam sandblasting" system is described below in which a bubble foam laden with abrasive is propelled through a small nozzle. The system has very specific applications in the dental industry for 1) general cleaning of teeth such as removal of tobacco, tea and other stains; 2) for selectively abrading away carious enamel, 3) cleaning prosthodontic restorations, 4) abrading various tooth and restorative materials in preparation for bonding, and 5) periodontal pocket cleaning with osteophylic abrasives; 6) cleaning of occlusal pits and fissures for sealing. In addition, the system has numerous applications in cleaning and etching materials in the jewelry, semi-conductor, automotive and other industries.

The principle technical tasks of this invention are to develop an improved method and apparatus to provide the optimum mixture of a high pressure foam (gas, air, water, and sudsing agent) and abrasive particles so as to decrease cleaning and abrading time, reduce deflection of the abrasive foam stream and minimize the volume of materials needing removal during or upon completion of cleaning. The disclosed invention seeks to accomplish all of the referenced improvements. The physical operation of the invention involves bubbling air through a mixture of liquid (water), abrasive solid particles (aluminum oxide, sodium bicarbonate, hydroxylapatite, etc.), with a pleasant flavoring agent and a wetting agent(sudsing agent) thereby creating a foam. Abrasive particles are caused to adhere onto the surfaces and interfaces of the rising bubbles by the suitable choice of a surface active flocculating agent. The abrasive carrying foam is then propelled through a small nozzle to produce the "wet foam sandblasting" mist.

Applicant notes that the disclosed method and apparatus are not intended to disperse a slurry or froth but rather a foam. Applicant references and incorporates commonly accepted definitions of the terms slurry, froth and foam (see Perry's Handbook of Chemical Engineering, pages 18-60). A slurry is predominantly a mixture of liquid and solid particles where the liquid is a composition such as water. A foam is generally formed when bubbles rise to the surface of a liquid and persist for a while without coalescence with one another or rupture into the vapor space. A froth is distinguished as a highly concentrated dispersion of bubbles contained within a liquid.

By utilizing air bubbles coated with a mixture of liquid and abrasive particles as a means to transport abrasive particles to a cleaning surface, the efficiency of the cleaning process is increased by providing an optimum mixture of abrasive particles in the high pressure foam. Additionally since the abrasive is coated with a liquid prior to be dispersed, the disclosed apparatus eliminates the potential for a patient inhaling airborne abrasive particles. Foam bubbles contain a small percentage of liquid volume as compared to the total foam volume, which is generally less than one percent water by volume. Thus when the foam is propelled through the sandblaster nozzle there is no massive water splattering and needed clean-up. Another advantage of the disclosed invention is that sub-micron particles may be used in the sandblaster thereby providing the user with the ability to clean smaller pits and fissures than is presently possible with existing sandblasters.

Another anticipated benefit of the disclosed invention is that since the abrasive particles are mixed with a liquid prior to being propelled, they contain more mass than dry particles and therefore disperse more kinetic energy.

BRIEF DESCRIPTION OF THE DRAWINGS

The method and apparatus is described in greater detail in the text that follows, with the aid of the accompanying diagrams and drawings, wherein:

FIG. 1 is a drawing illustrating the method disclosed in the invention.

FIG. 2 shows in a typical detail view the gaseous bubbles as they are dispersed through the mixture of liquid, wetting agent and abrasive particles.

FIG. 2a shows in detail view the abrasive laden foam.

DESCRIPTION OF THE PREFERRED EMBODIMENTS

Figure 3:
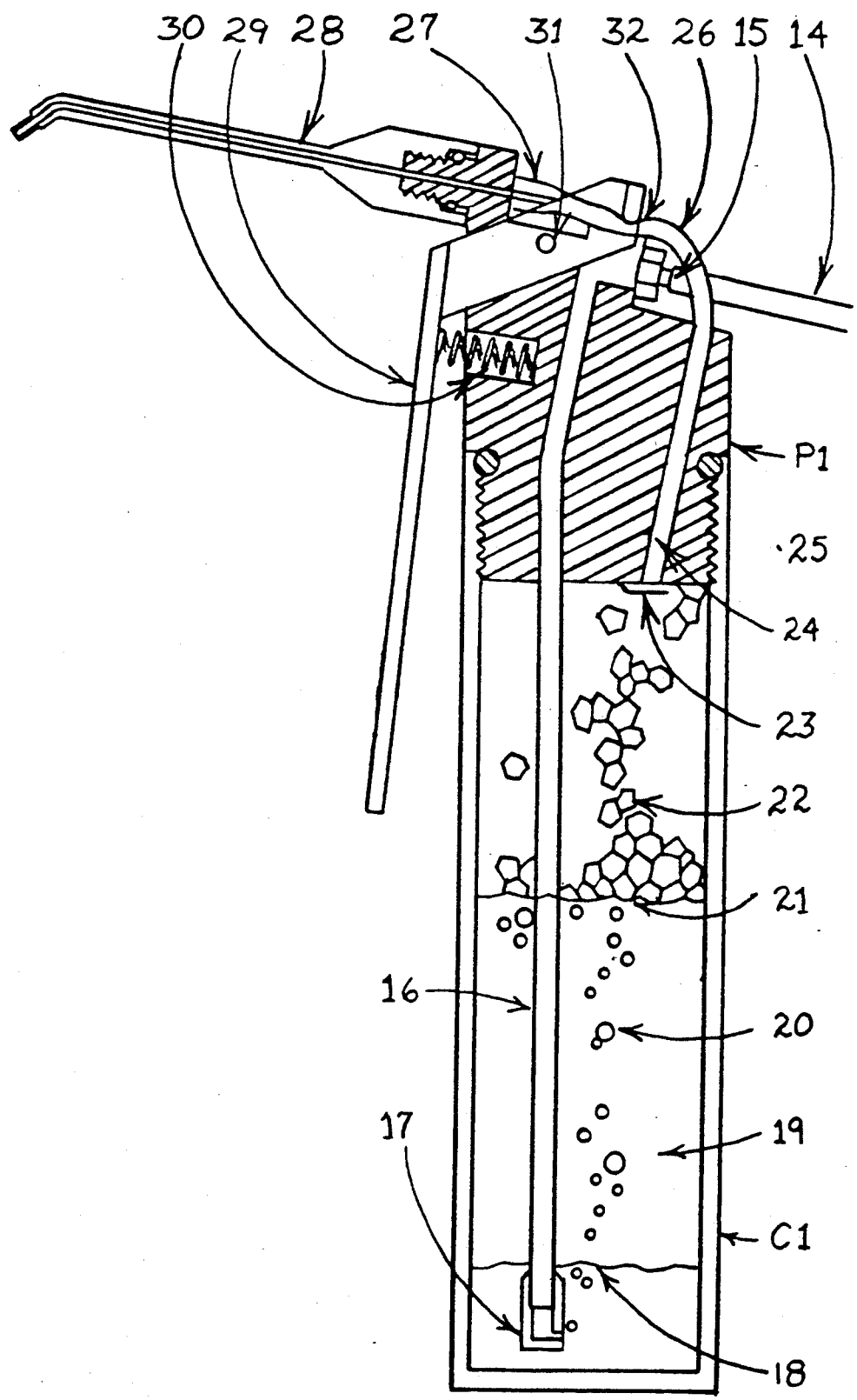
FIG. 3 shows in a sectional view the preferred embodiment of the disclosed apparatus.

Referring to the drawings, and particularly to FIG. 1 is illustrated a method for cleaning teeth as well as the numerous other applications as already described in the background of the invention section. The physical operation of the invention involves discharging a compressed gas (typically air) through a gas sparger 3 in a pressurized chamber P1 through a mixture of liquid(typically water) and a wetting agent(such as sodium lauryl sulfate) 5, and abrasive solid particles 4 (aluminum oxide, calcium phosphate, sodium bicarbonate, etc.), thereby creating a foam 6, under pressure. The abrasive laden foam is then propelled by a differential pressure out of the pressure vessel and through a tube 8 and discharged through a small nozzle 10 to produce the "wet foam sandblasting" stream. A valve or other similar device is provided as a means to control the flow of the exiting abrasive laden foam.

Air passing through the gas sparger serves two purposes. First, the air bubbles facilitate and activate blending of the abrasive powder and liquid to create a slurry. Secondly, the passage of air bubbles through the liquid slurry results in the production of foam. Bubbles rising through the slurry help to maintain a suspension of the solid abrasive in the liquid. A homogeneous suspension of abrasive and liquid, although desired is however not necessary for the wet foam blasting mechanism to work effectively.

The gas sparger orifice size in combination with the gas flow rate, vessel size, and the viscosity, density and interfacial surface tension of both the liquid phase and the resulting foam affect the stability and size of the bubbles in the foam. The initial size of the bubble produced in the liquid phase at the tip of the sparger is largely determined by the orifice(s) diameter, liquid density and the interfacial tension of the gas and liquid film. For singularly produced bubbles from a sparger, empirical equations suggest that bubble sizes vary proportionally to the cube root of the orifice diameter. Accordingly the foaming characteristics of the orifice are fairly insensitive to the orifice size, unless a fritted filter type of gas disperser is substituted for an open orifice. In the preferred embodiment, discussed later, a foam with bubbles approximately ¼ inch in diameter is desired. A foam consisting of bubbles significantly less than 0.1 inches in diameter produces flow friction in the exit tubing(8) and nozzle(10) which diminishes the effectiveness and velocity of the exit stream. This, in turn restricts the ultimate blasting force of the sandblaster apparatus.

A foam is formed when gas bubbles pass through and rise to the surface of the liquid slurry and persist without coalescence with one another, or without rupturing into the vapor space above the liquid. The duration and sustenance of the foam is determined by and can be controlled by the physical chemical nature of the liquid and of the bubble laminae. For the wet foam sandblaster, the foam life needs to be only a few seconds; the residence time of the foam in the vessel is short under normal operating flows.

Abrasive particles are picked up by, and onto, the interface of the gas bubbles rising through the slurry. After the bubbles reach the surface, they retain the solid particles, either by adhesion onto the walls of the bubbles (which is the case for sub-micron particles), or are trapped in the boundary zone between adjacent bubbles (for larger particles). FIG. 2 illustrates in detail the typical physical relationship between the gas bubbles and the abrasive particles(11). As the varying size bubbles (12) pass through the mixture of water and wetting agent, the suspended particles become attached to the bubble surface and are carried into the foam. FIG. 2a illustrates how the abrasive particles are entrained and transported by the foam. By controlling the production and nature of the foam, the abrasive particle transport is concomitantly controlled.

The duration and stability of a foam is a function of the existence of a surface skin of relatively low interfacial tension immediately overlying a solution bulk of higher surface tension. A high skin tension of the bubbles favors the coalescence and disappearance of the foam. This is why a pure liquid will seldom sustain a foam, because there is no difference in concentration between the surface and bulk of the solution. The phenomenon of surface elasticity resulting from differences between the bulk and surface of the liquid also accounts for the ability of bubbles to deform without collapsing as they enter the spray nozzle line. Once the foam has entered the nozzle line (8), however, collapse of the bubbles is not significant because of their high velocity in the small tubing. As the foam travels the nozzle line, the transport of each of the liquid, solid and gas phases is not dependant upon a bubble film mechanism; in fact, film interfaces now only create friction and impede the flow.

Finely divided, insoluble solids have the specific ability to stabilize foams. Particles on the order of 50 microns and smaller normally extend foam life. This is consistent with the theory that solid particles of medium contact angle with the liquid will prevent the coalescence of two bubbles with which it is in simultaneous contact.

The viscosity of the liquid in a bubble retards the coalescing of adjacent bubbles by retarding the drainage or bubble thinning process. The higher the viscosity, the slower will be the foam disappearance. A thin walled bubble will often have an effective viscosity higher than the bulk of the parent liquid. This is a self-correcting aid to foam stability because as drainage thins the bubble wall, the drainage rate decreases. Finely suspended solids trapped in the interface between bubbles produce increases in viscosity. Therefore, the described particle flotation or entrainment mechanism for wet foam sandblasting is inherently self-stabilizing.

The "floatability" of an abrasive particle in a slurry to form a foam is essentially a property of the solid particle; some particles are more floatable than others, depending upon their size, density, and chemical composition. Moreover, floatability is mainly a surface phenomenon; the nature of the film on the outside of the particle is the controlling factor. It is assumed that the liquid media for the sandblasting will normally be water. Thus, for any particular abrasive grain, there will be selective choices of surface active agents to add to the water. The amounts of additive will be determined by both the particle size and the characteristics of the subsequent foam.

The choice of surface active agent, (called collector reagent in the mineral flotation industry), will depend upon whether the abrasive is filmed and floated by a cationic reagent or a anionic reagent. A cationic reagent has a positive ion charged active site. The ultimate effectiveness of any flotation aid will ultimately depend upon empirical experimentation. For intraoral application of the wet foam sandblasting, the flotation reagent must be non-toxic and proven safe.

Chemical compounds other than the collector reagent may be added to the liquid phase for special purposes. Medical applications of wet sandblasting may indicate any number of the following: Antibiotics, Antiseptics, Astringents, acids/bases, selective dyes, etc.

The solid components of the slurry described up to this point have been identified as abrasives. The application of the device for purposes other than abrasion should also be mentioned. For example, solid particle hydroxyapatite or mixed particles of calcium phosphate might be propelled so as to be imbedded into a tissue, tooth or bone structure for the purpose of sealing tooth dentin or to stimulate ligament attachment.

Referring next to FIG. 3, the preferred embodiment of the apparatus disclosed in FIG. 1 and the accompanying text is shown. The apparatus is designed for cleaning, abrading and polishing teeth or the surface of other materials. The apparatus comprises a hollow elongated pressurized canister C1 which constitutes a handle and includes a blasting head P1 which constitutes a handle and includes a blasting head P1 which contains a nozzle assembly 28 at one end of the blasting head P1, an air receiving member 15 at the other end of the blasting head P1, and a pinch lever 29 as a means to control the flow of foam. The air receiving member 15 can be designed in numerous ways. In the embodiment shown in FIG. 3, the air receiving member 15 is a commercially available fitting comprising one threaded end provided as a means to engage inner threads in the blasting head P1 in order to be affixed to the blasting head P1. The other end of the air receiving member provides a barbed fitting over which the inner diameter of a commercially available plastic air supply tube 14 will slide over and become engaged.

It is envisioned for application in the dental industry the supply of gas 14 (typically air) will emanate directly from an existing standard dental operatory. Experimentation with the apparatus has shown that the range of air pressure supplied should vary between 20 and 120 pounds per square inch. Variance of the pressure between 20 and 120 psi is found to optimize the particular application and can be selected by the user. The canister holding the abrasive slurry and foam is designed to operate under pressure, consequently there needs to be a check valve on the incoming air line. This check valve must be capable of holding back a liquid containing abrasive particles, not just a gas pressure. The current design uses a rubber O-ring which is "captured" by the two piece holder. A stainless steel ball, under spring compression, seats against the O-ring. This design prevents abrasive particles from becoming lodged under the O-ring and leaking.

Returning to the apparatus depicted in FIG. 3, there is a passage tube 15a through the blasting head P1 which is provided as a means to transport the pressurized air into the pressurized canister C1. An air supply line 16 is connected to the blasting head P1 and connects the air passage tube 15a to allow pressurized air to be transported to the gas sparger 17 without interruption. The air supply line 16 should be fabricated from a rigid metal or plastic to ensure non-deflection during operation. At the opposite end of the supply tube from the blasting head is a gas sparger 17. Design and operation of the gas sparger 17 has been thoroughly discussed in the text accompanying FIG. 1.

The process of entraining abrasive or other particles in the bubbles 20 and foam 22 has generally been described in the text accompanying FIG. 1 and are incorporated herein by reference. Initial loading of the liquid, wetting agent and abrasive particles is accomplished by separating the blasting head P1 from the canister C1. In the preferred embodiment, outside threads of the blasting head P1 interface inside threads on the canister C1 and provide a means to secure the canister C1 to the blasting head P1. A commercially available rubber O-ring 25 is located as depicted in FIG. 3 and is provided as a means to seal the inner volumetric space of the canister C1 to allow the inner volume pressure to be increased beyond standard atmospheric pressure. The O-ring also provides a means to contain the liquid, abrasive and foam and prevent spillage. Following separation of the canister C1 from the blasting head P1, water, wetting agent and abrasive or other particles as previously described may be placed in the canister C1. For general tooth cleaning two teaspoons of abrasive particles 18, one milliliter of surface active (foaming or wetting) agent and water 19 to fill approximately two thirds of the canister's 21 volumetric space is supplied. The canister C1 is then screwed onto the blasting head P1. After the canister is securely affixed to the blasting head and the O-ring 25 is engaged, the user by hand can shake the apparatus as a means to encourage initial mixing of the water, wetting agent and abrasive particles. Shaking by hand, however, is unnecessary during operation of the apparatus; rising bubbles will accomplish the same result.

Returning to the apparatus in FIG. 3 an exit passage 24 is shown which is located in the blasting head P1. The exit tube 24 is formed by using a drill or other commercially available means to bore the tube 24 through the blasting head P1. At the end of the tube 24 farthest from the inner volume of the canister C1, a receiving member 24a is affixed to the blasting head P1 and is provided as a means to connect a commercially available plastic foam tube 26 to the nozzle assembly. The foam tube 26 is connected to the exit nozzle assembly 28 and provides a means of containing and directing the foam as it is expelled from the canister C1 to the exit nozzle assembly 28. The foam tube 26 is connected to the blasting head at a location which accepts the nozzle assembly 28 at one end and the foam tube 26 at the other end and provides a passage by which the foam can be transported from the foam tube 26 to the nozzle assembly 28.

Figure 4:
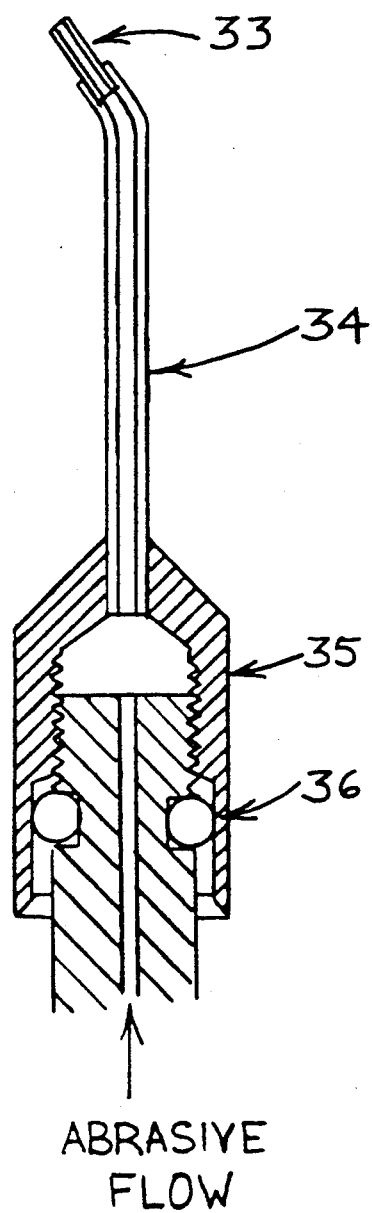
FIG. 4 shows a detail view of the nozzle which directs the exiting abrasive laden foam.

The nozzle assembly 28 provides a means to discharge and direct the flow of abrasive laden foam. The nozzle assembly is shown in more detail in FIG. 4. The assembly 28 is comprised of a nozzle base 35 capably of holding a nozzle stem tube 34. Although numerous configurations are possible, in the preferred embodiment, the nozzle stem tube 34 is bent at an approximately 45 degree angle in order to increase the number of locations in the human mouth where the apparatus may be used. At the bent end of the nozzle stem 34, a nozzle tip 33 (preferably from tungsten carbide) is secured to the inner diameter of the nozzle stem. The contra-angled nozzle 34 on the wet foam blaster may be swiveled 360 degrees with a simple twist of the nozzle base 35. By this means the spray of foam may be pointed in an increased number of directions. The nozzle assembly 28 may be removed from the wet foam blaster by twisting the nozzle base 35 counter clockwise approximately three turns. As depicted in FIG. 4, a commercially available rubber O-ring 36 is shown. The O-ring 36 captured inside the nozzle housing 35 prevents leakage until the assembly is fully removed, thereby allowing the nozzle assembly 28 to be swiveled without causing any leakage of foam.

The nozzle assembly 28 may be removed simply and quickly by unscrewing it counter clockwise, making it convenient for interchanging nozzles and for autoclaving of the nozzle between uses. The captured O-ring 36 remains affixed on the blasting head P1.

The flexibility for different sandblasting applications is built into the wet blaster by configuring the apparatus with a different nozzle assembly 28. Changing from a jet stream of tiny-particle abrasive foam to a sharp blast of a polishing compound may be done in a matter of seconds by using nozzle assemblies made of different materials and varying diameters. A tungsten carbide tipped nozzle piece may be attached for cutting with hard abrasives such as silicon carbide.

Referring once again to FIG. 3, a pinch lever valve assembly 29 is shown which provides a means to control the flow of abrasive laden foam. In a closed position, the pinch lever valve 29 prevents the abrasive laden foam from entering the nozzle assembly 28. This operation limits the dead flow time for the foam to reach the nozzle assembly 28. The canister C1 holding the foam and slurry remains under pressure when the pinch lever 29 is released. The lever assembly 29 operates on the simple physical principle of mechanical leverage. A pivot point 31 is positioned in the blasting head P1 to which the pinch lever 29 is affixed. To open the pinch lever, human hand force overcomes the force applied by a spring 30 and allow the foam tube 26 to return to its original shape thereby allowing the passage of foam. When hand pressure is released, the spring 30 through mechanical leverage pinches the foam tube 26 stopping the flow of foam. When the air supply pressure is turned off or disconnected, the canister may be depressurized by depressing the pinch lever valve.

We claim:

1. An apparatus for cleaning and etching teeth and other surfaces comprising:
   a canister capable of being sealed and pressurized and holding a pre-determined mixture of liquids, abrasive particles, and wetting agent, said canister also having a means for dispersing a stream of pressurized gas through the mixture of liquid, particles, and wetting agent causing thereby a formation of foam and urging the abrasive particles to become entrained into the foam,
   a means to direct the abrasive laden foam exiting the cansiter to the surface to be cleaned comprising a deformable tube integrally connected to the canister at one end and a rigid exit orifice nozzle at the other end,
   a means to control the flow of abrasive laden foam integral with the foam direction means, wherein the control means comprises a pinch lever which on one end contact and pinches closed the deformable foam tube, a pivot point attaching the pinch lever to the canister and a spring which applies force to the pinch lever to urge the pinch lever to deform the tube to a degree sufficient to stop the flow of foam.

2. An apparatus for cleaning and etching teeth and other surfaces comprising:
   a canister capable of being sealed and pressurized and holding a pre-determined mixture of liquids, abrasive particles, and wetting agent, said canister also having a means for dispersing a stream of pressurized gas through the mixture of liquid, particles, and wetting agent causing thereby a formation of foam and urging the abrasive particles to become entrained into the foam,
   a means to direct the abrasive laden foam exiting the canister to the surface to be cleaned comprising a deformable tube integrally connected to the canister at one end and a rigid exit orifice nozzle at the other end, and
   a means to control the flow of abrasive laden foam integral with the foam direction means.

3. The apparatus of claim 2, comprising a contra-angle detacheable nozzle assembly as a means to direct the abrasive laden flow.

4. The apparatus of claim 2, comprising a nozzle assembly as a means to direct the abrasive laden froth which can be autoclaved.

5. The apparatus of claim 2, wherein sub-micron sized abrasive particles can be used.

6. The apparatus of claim 2, wherein the means to control the flow of abrasive laden froth comprises a mechanical valve or other similar device.

7. The apparatus of claim 2, wherein the apparatus is stationary and comprises a means to direct the abrasive laden froth which is remotely connected.

8. The apparatus of claim 2, wherein the control means comprises a pinch lever which on one end contact and pinches closed the deformable foam tube, a pivot point attaching the pinch lever to the canister and a spring which applies force to the lever to urge the lever to deform the tube to a degree sufficient to stop the flow of foam.

9. A method for cleaning teeth and other surfaces, comprising the steps of:
   a) placing a mixture of liquid, abrasive particles and a surface tension reducing agent into a canister and sealing the canister;
   b) dispersing gas through the mixture of liquid, abrasive particles and sudsing agent having the effect of the bubbles carrying the abrasive particles on the surface and interfacial areas of said bubbles, thereby creating a foam of wetted abrasive laden bubbles within the canister;
   c) dispersing the abrasive laden foam from an exit passage in the canister;
   d) and directing the abrasive laden foam toward the surface to be cleaned.

10. The method of claim 9, wherein the liquid is water, the abrasive particles are as tiny as 0.01 microns in diameter, and the surface tension reducing agent is a composition such as alcohol or sodium lauryl sulfate.

* * * * *